United States Patent
Tang et al.

(10) Patent No.: US 9,216,169 B2
(45) Date of Patent: Dec. 22, 2015

(54) PHARMACEUTICAL COMPOSITION COMPRISING CANDESARTAN OR ESTER THEREOF AND CHLORTALIDONE, AND USE THEREOF

(71) Applicant: TIANJIN INSTITUTE OF PHARMACEUTICAL RESEARCH, Tianjin (CN)

(72) Inventors: Lida Tang, Tianjin (CN); Zhuanyou Zhao, Tianjin (CN); Weiting Wang, Tianjin (CN); Wengong Xi, Tianjin (CN); Chunhua Hao, Tianjin (CN); Xiangwei Xu, Tianjin (CN); Bing Yu, Tianjin (CN)

(73) Assignee: TIANJIN INSTITUTE OF PHARMACEUTICAL RESEARCH, Tianjin (CN)

( * ) Notice: Subject to any disclaimer, the term of this patent is extended or adjusted under 35 U.S.C. 154(b) by 0 days.

(21) Appl. No.: 14/367,961

(22) PCT Filed: Dec. 21, 2012

(86) PCT No.: PCT/CN2012/087177
§ 371 (c)(1),
(2) Date: Jul. 18, 2014

(87) PCT Pub. No.: WO2013/091574
PCT Pub. Date: Jun. 27, 2013

(65) Prior Publication Data
US 2015/0011598 A1 Jan. 8, 2015

(30) Foreign Application Priority Data
Dec. 23, 2011 (CN) .......................... 2011 1 0437755

(51) Int. Cl.
*A61K 31/41* (2006.01)
*A61K 31/4184* (2006.01)
*A61K 31/4035* (2006.01)

(52) U.S. Cl.
CPC ......... *A61K 31/4184* (2013.01); *A61K 31/4035* (2013.01)

(58) Field of Classification Search
USPC .......................................................... 514/381
See application file for complete search history.

(56) References Cited

U.S. PATENT DOCUMENTS

| | | | | |
|---|---|---|---|---|
| 5,250,548 A | * | 10/1993 | Winn et al. | .................... 514/340 |
| 2007/0160665 A1 | * | 7/2007 | Brand et al. | ................... 424/464 |
| 2010/0204252 A1 | * | 8/2010 | Kupfer | ........................ 514/264.1 |
| 2011/0008428 A1 | * | 1/2011 | Mhase et al. | .................. 424/464 |
| 2012/0034272 A1 | | 2/2012 | Kuhl et al. | |

FOREIGN PATENT DOCUMENTS

| CN | 102227216 A | 10/2011 |
|---|---|---|
| WO | 2005014043 A1 | 2/2005 |
| WO | 2010075347 A2 | 7/2010 |

OTHER PUBLICATIONS

International Search Report PCT/CN2012/087177{KIPO} dated Mar. 28, 2013.

* cited by examiner

*Primary Examiner* — Rei-Tsang Shiao
(74) *Attorney, Agent, or Firm* — Edwin S. Flores; Chainey P. Singleton; Chalker Flores, LLP

(57) ABSTRACT

Provided is a pharmaceutical composition comprising candesartan or ester thereof and chlorthalidone, and use thereof, wherein the weight ratio of candesartan or ester thereof to chlorthalidone is 5.3:1 to 1:6.25. The pharmaceutical composition has a synergistic antihypertensive effect, and can enhance the antihypertensive effect and extend duration of antihypertension.

5 Claims, 1 Drawing Sheet

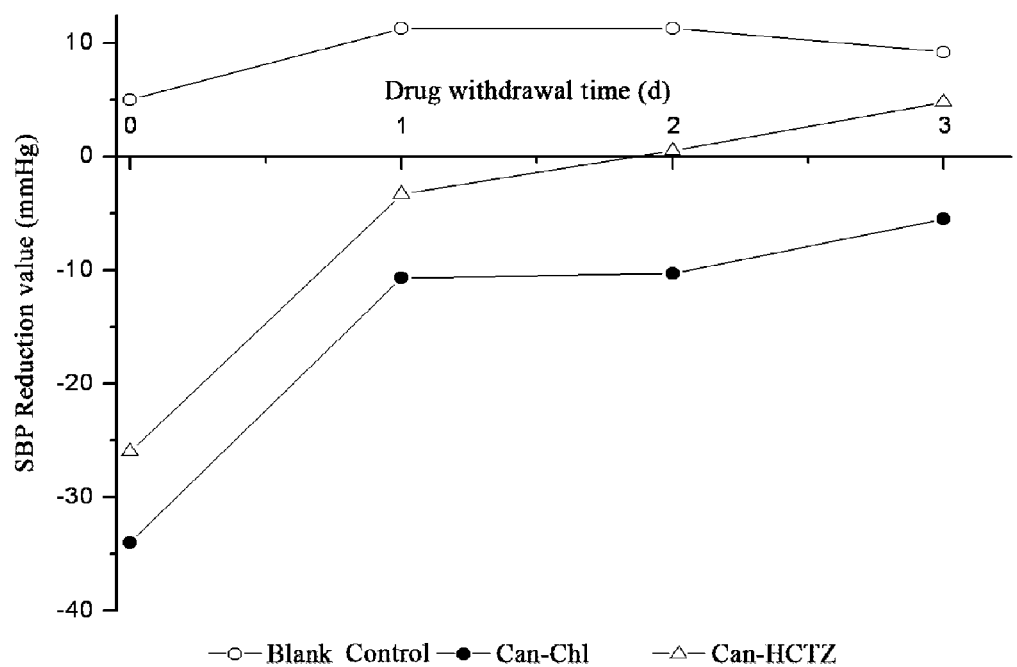

PHARMACEUTICAL COMPOSITION COMPRISING CANDESARTAN OR ESTER THEREOF AND CHLORTALIDONE, AND USE THEREOF

TECHNICAL FIELD

The present invention relates to a pharmaceutical composition comprising candesartan or ester thereof and chlorthalidone, use of the pharmaceutical composition in the preparation of antihypertensive medicines and use of candesartan or ester thereof and chlorthalidone in the preparation of antihypertensive medicines, and a method for treating hypertension.

BACKGROUND ART

Hypertension or high blood pressure is a common cardiovascular disease. Recently, the prevalence rate of hypertension is increasing constantly. According to the newest diagnostic criteria of the World Health Organization (WHO), the prevalence rate of hypertension is about 18.8% of residents aged above 18 years old in China and there are at least more than 200 million patients with hypertension throughout the country, while the number of people with hypertension is more than 960 million throughout the world. Hypertension can cause significant increase in prevalence and hazard rates of complications such as stroke, coronary heart disease, heart failure, kidney disease, large arterial and peripheral arterial disease, etc. The premature deaths resulting from the hypertension rising are up to 1.5 million people each year in China Patients with hypertension constitute 41% of the total chronic outpatients, which occupies the first place in the country. The medical expenses for hypertension are up to 40 billion yuan each year. Therefore, it is significant to prevent and cure hypertension and control the complications resulting from it.

WHO requires that the patients with hypertension need to constantly take medicines throughout their lifetime. Although there are currently many kinds of anti-hypertension drugs, the prevention and treatment for hypertension, prediction of efficacy, and control of complication and hazard fail to reach the desired requirements. Thus, the task for the prevention and treatment of hypertension is still arduous in our country. Combination therapy is a direction of treating hypertension, which helps to interfere with multiple blood pressure-maintaining mechanisms, eliminate genetic individual differences in response to drugs, add or supplement pharmacological action and neutralize adverse reactions resulting from different drugs, thus reduce the dosages of a single drug and decrease the adverse reactions, so as to better protect the target organs and increase patient compliance. Modern studies have indicated that the combination use of drugs with different mechanism of action can increase the efficiency of the treatment of hypertension to 80-90%, which is higher than the efficiency of the treatment with each of the drugs alone (40-60%). The combination of angiotensin II receptor antagonists (ARBs) (sartans) with diuretics is a common combination of drug compound in clinical treatment. Among the currently common used ARBs, candesartan has significant advantages in antihypertensive efficacy. Research data shows that the inhibitory effect of candesartan on AT1 receptor is the strongest, and the inhibitory effect of candesartan on vasoconstriction caused by angiotensin is also the strongest. Compared with other antihypertensive drugs, candesartan is safer and has more definite effect than calcium antagonist, thiazide diuretic and ACEI. However, candesartan also has disadvantages that its effectiveness is no longer increase when the dosage thereof has been increased to a certain level. Therefore, it is needed to combine candesartan with other antihypertensive drugs to achieve the purpose of effectively lowering the blood pressure in the treatment of many patients.

The diuretic hydrochlorothiazide lowers the blood pressure by enhancing sodium excreting of kidney out of the body. Hydrochlorothiazide may produces synergetic effect with candesartan, and the mechanism is that the diuretic can activate the rennin-angiotensin system (RAS), which makes the change of blood pressure more dependent on RAS, and thus enhancing the antihypertensive effect of candesartan and meanwhile compensating for the disadvantage of activating RAS caused by using hydrochlorothiazide alone. Furthermore, hydrochlorothiazide may also cause hypokalemia when it is used alone, and the dosage of hydrochlorothiazide can be lowered to reduce the occurrence of hypokalemia when it is used in combination with candesartan. Currently, candesartan cilexetil/hydrochlorothiazide compound has already come to the market.

In recent years, the clinical position of the diuretic chlorthalidone is re-recognized. Compared with hydrochlorothiazide, chlorthalidone has longer half-life, which results in an enduring antihypertensive effect, especially chlorthalidonein the night. Clinical studies show that chlorthalidone 12.5-25 mg/d of chlorthalidone and 25-50 mg/d of hydrochlorothiazide lower 24-hour blood pressure by 12.4 and 7.4 mmHg respectively, and lower the night-time blood pressure by 13.5 and 6.4 mmHg respectively. It can be seen that chlorthalidone has a greater advantage in antihypertensive effect. Khoska believes that the effect of chlorthalidone on reducing the systolic blood pressure (SBP) is better than that of hydrochlorothiazide, as the antihypertensive efficacy of chlorthalidone is about 1.5-2 times of that of hydrochlorothiazide, and chlorthalidone has a longer action time. Thus, when blood pressure control is not ideal, chlorthalidone, rather than hydrochlorothiazide, should be first used. Clinical studies indicate that the valid control rates of blood pressure of chlorthalidone, amlodipine and lisinopril are 68.2%, 66.3% and 61.2% respectively. Chlorthalidone is better than amlodipine in the prevention of heart failure, and is better than lisinopril in the prevention of stroke. The clinical study on the compound composed of azilsartan and chlorthalidone has been performed. The results of the study on this compound in 1714 patients show that the compound of "azilsartan+chlorthalidone" is better than the compound of "olmesartan+hydrochlorothiazide" in the effect of reducing SBP, and the compound of "azilsartan+chlorthalidone" can reduce the SBP by 22.9-29.8 mmHg compared with the basic value, whereas single azilsartan reduces the SBP by 12.1-15.9 mmHg compared with the basic value and single chlorthalidone reduces the SBP by 12.7-15.9 mmHg compared with the basic value. Thus, it can be seen that the compound of azilsartan+chlorthalidone has a greater advantage.

SUMMARY OF THE INVENTION

Therefore, the inventor of the present invention has studied the compound antihypertensive drugs comprising chlorthalidone. Specifically, based on current treatment for hypertension and research and development background of the new drugs, the inventor has studied different ratios of candesartan or ester thereof combined with chlorthalidone in detail. It has been found that the compound has antihypertensive effect and the candesartan or ester thereof and chlorthalidone have synergistic effect within a specific ratio, which provide a guidance for the research and development of antihypertensive drugs.

In one aspect, the present invention provides a pharmaceutical composition comprising candesartan or ester thereof and chlorthalidone as active ingredients, wherein the weight ratio of candesartan or ester thereof to chlorthalidone is 5.3:1 to 1:6.25.

In another aspect, the present invention provides the use of candesartan or ester thereof and chlorthalidone in the preparation of antihypertensive drugs.

In yet another aspect, the present invention provides the use of the said pharmaceutical composition in the preparation of antihypertensive drugs.

In still another aspect, the present invention provides a method for treating hypertension comprising administering the said pharmaceutical composition to a patient in need of the treatment.

When the ratio of candesartan or ester thereof to chlorthalidone is in the range of 5.3:1 to 1:6.25, the pharmaceutical composition comprising candesartan or ester thereof and chlorthalidone has synergistic antihypertensive effect and is able to increase efficacy, enhance the antihypertensive effect and extend the effective antihypertensive time. Using the pharmaceutical composition having such a ratio of candesartan or ester thereof to chlorthalidone can decrease the dosage of drugs and reduce the side effects so as to be beneficial to the treatment of hypertensive diseases.

DETAILED DESCRIPTION OF THE DRAWINGS

The present invention is now described in detail with reference to the following drawings, in which:

FIG. 1 shows the comparative result of the effect of the compound of Can-Chl of the present invention with that of the control compound of Can-HCTZ on SBP after continuous administration for 1-14 days and stopping medication for 3 days in Example 13.

DETAILED DESCRIPTION OF THE INVENTION

The disclosure of the present invention is now described specifically in connection with the purpose of the present invention.

After studying on candesartan or ester thereof and chlorthalidone, the inventor of the invention has found that it has significant synergistic effect when the ratio of candesartan or ester thereof to chlorthalidone is in the range of 5.3:1 to 1:6.25.

According to the pharmaceutical composition of the present invention, wherein the weight ratio of candesartan or ester thereof to chlorthalidone is preferably 1.28:1 to 1:6.25, and more preferably 1.28:1 to 1:3.125.

The weight ratio of candesartan or ester thereof to chlorthalidone may also be preferably 1:1 to 1:6.25.

In a preferred embodiment of the present invention, the weight ratio of candesartan or ester thereof to chlorthalidone is preferably 1.28:1 or 1:1.5 to 1:6.25, and most preferably 1.28:1 or 1:1.5 to 1:3.125.

According to the pharmaceutical composition of the present invention, wherein the ester of candesartan can be various esters of candesartan, such as candesartan cilexetil purchased from Department of Modern Chemical Pharmaceutical, Tianjin Institute of Pharmaceutical Research. It is generally believed in the art that "candesartan" or "the ester of candesartan" refers to candesartan cilexetil. Therefore, in the present invention, the weight of candesartan or ester thereof is all by weight of candesartan cilexetil. Specifically, the structure of candesartan cilexetil is show as formula I.

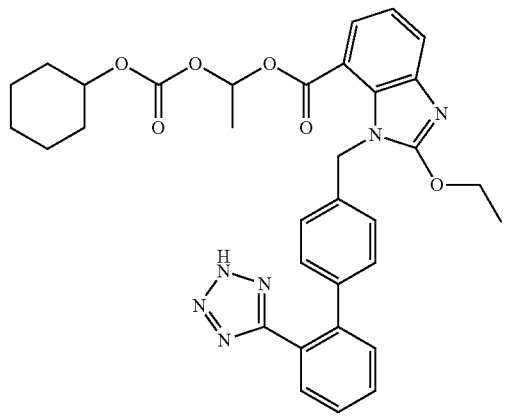

I

In another aspect, the present invention provides the use of candesartan or ester thereof and chlorthalidone in the preparation of antihypertensive drugs. Based on the characteristics of clinical medication, such as drug effects and possible side effects, the weight ratio of candesartan or ester thereof to chlorthalidone may be 5.3:1 to 1:6.25, preferably 1.28:1 to 1:6.25, more preferably 1.28:1 to 1:3.125; or preferably 1:1 to 1:6.25, or preferably 1.28:1 or 1:1.5 to 1:6.25, and most preferably 1.28:1 or 1:1.5 to 1:3.125. When candesartan or ester thereof and chlorthalidone are used in the antihypertensive drugs, the amount of candesartan or ester thereof may be 2 to 16 mg, preferably 2 to 8 mg, and the amount of chlorthalidone may be 4 to 25 mg, and preferably 6 to 12.5 mg in each unit dose of drug.

In yet another aspect, the present invention provides the use of the said pharmaceutical composition in the preparation of antihypertensive drugs. When used in the antihypertensive drugs, the amount of candesartan or ester thereof may be 2 to 16 mg, preferably 2 to 8 mg, and the amount of chlorthalidone may be 4 to 25 mg, and preferably 6 to 12.5 mg in each unit dose of drug.

In still another aspect, the present invention provides a method for treating hypertension comprising administering the pharmaceutical composition to a patient in need of the treatment.

According to the method for treating hypertension of the present invention, preferably, the administration dosage of candesartan or ester thereof is 0.057 to 0.228 mg/kg per day, and the administration dosage of chlorthalidone is 0.089 to 0.357 mg/kg per day. Generally, for an average adult, the above administration dosage corresponds to 4 to 16 mg of candesartan or ester thereof per day, and chlorthalidone 6.25 to 25 mg of chlorthalidone per day.

The pharmaceutical composition of the present invention may also comprise pharmaceutically acceptable carriers or excipients. Any common carriers or excipients in the art may be used in the pharmaceutical composition of the present invention as long as they do not adversely affect the active ingredients of the pharmaceutical composition of the present invention. In addition, the pharmaceutical composition of the present invention can be prepared into various dosage forms such as tablets, granules, solutions, capsules, powders and the like using common methods in the art.

Best Mode for Carrying out the Invention

The present invention is now further described with reference to the Examples. It should be noted that the following Examples are only used for illustrating rather than limiting the scope of the present invention. Any variations to the present invention made by a person skilled in the art according to the teachings of the present invention shall fall within the scope claimed in the claims of the present application.

Materials, Equipments and Methods Used in the Examples are Described as Follows.

In the Examples of the present invention, the ester of candesartan refers to candesartan cilexetil.

I. Drugs

Candesartan cilexetil (called Can for short), provided by the Department of Modern Chemical Pharmaceutical, Tianjin Institute of Pharmaceutical Research, is white powder, and the Batch No. is 20110604. Can is prepared with 0.5% sodium carboxymethyl cellulose (CMC) and is used for intragastric administration in rat.

Chlorthalidone (called Chl for short), provided by Wako Pure Chemical Industries, Ltd., is white powder, 25 g/vial. Its purity is more than 97% (HPLC), and the Batch No. is LDJ7832. Chl is prepared with 0.5% CMC and is used for intragastric administration in rat.

Hydrochlorothiazide (HCTZ) is purchased from Sigma Company of America.

II. Animals

Spontaneously hypertensive rats (SHR), male, are provided by Beijing Vital River Laboratory Animal Technology Co., Ltd. The number of animal production license is SCXK (Jing) 2007-0001. Animals are raised in an observation room at the room temperature of 25±2° C. controlled by central air-conditioning system and with artificial lighting of 12 h/day. The animals are raised in separate cages sized 43×27× 18 cm with 4 animals for each cage. The rats are free access to water and are fed with block fodder everyday, and the water supply is refreshed once a day. The temperature of the room for measuring the blood pressure is 26±2° C.

III. Apparatus

BP-98A intelligence and non-invasive blood pressure monitor, a product of Japanese Softron Technology Co., Ltd.

IV. Blood Pressure Measurement of Rats

The blood pressure is measured by Tail-Cuff method and the hear rate is measured according to the pulse frequency. Animals are pre-trained for the blood pressure measurement for more than 2 weeks so as to adapt to the environment of measurement. Animals are placed in a isothermal bag at 37° C. to be prewarmed for 5 to 10 min for formal measurement. Blood pressures of the rats are measured from tail arteries for 2 to 3 times at rest states, and an average value is taken as each blood pressure measured value. All data are collected and preserved by a computer.

V. Grouping and Administration (1) Regarding Examples 1-7

SHRs with systolic blood pressures (SBPs) >190 mmHg are selected for experiment.

Rats are randomly divided into 14 groups according to their blood pressures with each group having 7 rats. Animals are fasted overnight and measured for the blood pressure of pre-administration at the day of experiment, and then administered drugs in accordance with the following method:

The blank control group is intragastrically administered 0.5% CMC;

The single-drug group is intragastrically administered candesartan (Can) or chlorthalidone (Chl), with the dosage of Can of 0.36 mg/kg and the dosages of Chl of 0.0675, 0.36, 0.54, 0.72, 1.125 and 2.25 mg/kg respectively;

The pharmaceutical composition is administered with 6 different doses (denoted by F1, F2, F3, F4, F5 and F6 respectively). Specifically, the ratios of the dosages of Can+Chl in all pharmaceutical compositions are:

F1: 0.36+0.0675 mg/kg;

F2: 0.36+0.36 mg/kg;

F3: 0.36+0.54 mg/kg;

F4: 0.36+0.72 mg/kg;

F5: 0.36+1.125 mg/kg;

F6: 0.36+2.25 mg/kg,

The administration volumes are all 5 ml/kg.

Rats are continuously administered for 8 days. SBPs are measured 2, 4, 8, 12 and 24 hours after the last administration. The area under blood pressure reduction-time curve from 0 to 24 h ($AUC_{0-24}$) and the maximum blood pressure reduction value are calculated.

(2) Regarding Examples 8-12

SHRs with systolic blood pressures (SBPs)>190 mmHg are selected for experiment.

Rats are randomly divided into 20 groups according to their blood pressures with each group having 8-10 rats. Animals are fasted overnight and measured for the blood pressure of pre-administration at the day of experiment, and then administered drugs in accordance with the following method:

The blank control group is intragastrically administered 0.5% CMC;

The single-drug group is intragastrically administered candesartan (Can) or chlorthalidone (Chl), with the dosage of Can of 0.1, 0.2, 0.4 mg/kg respectively and the dosage of Chl of 0.3125, 0.625, 1.25 mg/kg respectively;

According to the clinical single-drug specification, the ratios of Can+Chl are set as follows:

For the ratio of Can:Chl=1:6.25, one dose of 0.1+0.625 mg/kg is set;

For the ratio of Can:Chl=1:3.125, two doses of 0.2+0.625 and 0.4+1.25 mg/kg are set;

For the ratio of Can:Chl=1:1.5625, two doses of 0.2+0.3125 and 0.4+0.625 mg/kg are set;

For the ratio of Can:Chl=1.28:1, one dose of 0.4+0.3125 mg/kg is set;

For the ratio of Can:Chl=2.56:1, one dose of 0.4+0.15625 mg/kg is set;

The administration volumes are all 5 mL/kg. Rats are continuously administered for 14 days. SBPs are measured 2, 4, 8, 12 and 24 hours after the first administration. On the day of 3, 7, 14 days after administration, the blood pressures are measured before administration and 5 hours after administration. Areas under blood pressure reduction-time curve from 0 to 24 h and from 0 to 14 days ($AUC_{0-24h}$, $AUC_{0-14d}$) are calculated.

(3) Regarding Example 13

SHRs with systolic blood pressures (SBPs) >200 mmHg are selected for the experiment.

Rats are randomly divided into 3 groups according to their blood pressures with each group having 6 rats. Animals are fasted overnight and measured for the blood pressure of pre-administration at the day of experiment, and then administered drugs in accordance with the following method (with a total dose of 1 mg/kg):

The blank control group is intragastrically administered 0.5% CMC;

According to the clinical single-drug specification, the ratios of Can+Chl are set as follows:

Can:Chl=1:1.5625 (clinical ratio of 8/12.5 mg):0.39+ 0.609375 mg/kg; Can/HCTZ=1:1.5625 (clinical ratio of 8/12.5 mg):0.39+0.609375 mg/kg;

The administration volumes are all 5 ml/kg. Rats are continuously administered for 14 days. SBPs are measured 1, 3, 5, 7, 12 and 24 hours after the first administration. On the day of 3, 7, 14 days after administration, the blood pressures are measured before administration and 5 hours after administration. Areas under blood pressure reduction-time curve from 0 to 24 h and from 0 to 14 days ($AUC_{0-24h}$, $AUC_{0-14d}$) are calculated.

VI. Analytical Method of the Measurement Results

The calculated results are expressed as mean±standard error ($\bar{x}\pm SE$); statistical treatment is performed using unpaired t test between groups to compare the significance of the average difference; the interaction between drugs are determined by using factorial analysis of variance, and $P<0.05$ means the difference has statistical significance.

EXAMPLE 1

Influence of 0.0675 mg/kg of Chlorthalidone and 0.36 mg/kg of Candesartan Cilexetil and Pharmaceutical Compositions Thereof on SBP The blank control group basically remains stable within 24 hours after the administration.

0.36 mg/kg of candesartan cilexetil takes effect 2 hours after oral administration, and it can significantly reduce SBP from 2 to 8 hours after oral administration.

0.0675 mg/kg of chlorthalidone has no significant antihypertensive effect after the administration.

The pharmaceutical composition 1 (F1) takes effect 2 hours after administration, and the effect may last 12 hours, the duration of antihypertension is significantly prolonged; the antihypertensive effect of F1 is better than that of candesartan cilexetil after administration for 24 hours and the antihypertensive effect of F1 is better than that of chlorthalidone after administration for 2 to 24 hours. Chlorthalidone and candesartan cilexetil have a synergistic effect in antihypertension after administration for 24 hours (P=0.036), and the results are shown in Table 1.

TABLE 1

($\bar{x} \pm SE$, n = 7)

| Group | Dosage (mg/kg) | Basic value | Pre-admin-istration | After administration (h) | | | | |
|---|---|---|---|---|---|---|---|---|
| | | | | 2 | 4 | 8 | 12 | 24 |
| Blank | — | 205 ± 3 | 209 ± 4 (3.6 ± 2.8) | 205 ± 4 (0.1 ± 2.2) | 206 ± 6 (0.7 ± 3.2) | 204 ± 5 (−1.6 ± 3.1) | 207 ± 4 (1.6 ± 3.0) | 206 ± 4 (0.6 ± 2.1) |
| Can | 0.36 | 203 ± 4 | 201 ± 3 (−2.0 ± 3.6) | 192 ± 4 (−11.0 ± 1.2**) | 185 ± 6 (−17.7 ± 2.9**) | 196 ± 3 (−7.3 ± 2.8) | 199 ± 3 (−3.7 ± 2.9) | 204 ± 3 (1.4 ± 0.7) |
| Chl | 0.0675 | 205 ± 6 | 208 ± 4 (2.3 ± 1.7) | 203 ± 5 (−2.1 ± 1.5) | 206 ± 5 (0.6 ± 2.3) | 204 ± 5 (−1.4 ± 1.3) | 203 ± 5 (−2.0 ± 1.8) | 207 ± 5 (2.1 ± 1.4) |
| F1 | 0.36 + 0.0675 | 208 ± 4 | 205 ± 4 (−2.7 ± 1.6) | 197 ± 3 (−11.0 ± 2.1*##) | 189 ± 5 (−19.3 ± 5.7*##) | 193 ± 7 (−14.7 ± 4.0*##) | 199 ± 5 (−9.6 ± 2.5*#) | 204 ± 5 (−3.7 ± 1.5++#) |

Notes:
1. Values in the brackets are the difference values compared with the basic value;
2. Compared with the blank control group, *P < 0.05, **P < 0.01;
3. Compared with Can, ++P < 0.01;
4. Compared with Chl, #P < 0.05, ##P < 0.01.

EXAMPLE 2

Influence of 0.36 mg/kg of Chlorthalidone and 0.36 mg/kg of Candesartan Cilexetil and Pharmaceutical Compositions Thereof on SBPs It still has an antihypertensive effect before administration of pharmaceutical composition 2 (F2), and after administration, the effect may last 24 hours, and the duration of antihypertension is significantly prolonged. Statistical analysis shows that chlorthalidone and candesartan cilexetil have a synergistic effect in the duration of antihypertension; the antihypertensive effect of F2 is better than that of candesartan cilexetil after administration for 8 to 24 hours and is better than that of chlorthalidone after administration for 2 to 24 hours. Statistical analysis shows that chlorthalidone and candesartan cilexetil have a synergistic effect in the degree of the blood pressure reduction after administration for 24 hours (P=0.0031), and the results are shown in Table 2.

TABLE 2

($\bar{x} \pm SE$, n = 7)

| Group | Dosage (mg/kg) | Basic value | Pre-admin- istration | After administration (h) | | | | |
|---|---|---|---|---|---|---|---|---|
| | | | | 2 | 4 | 8 | 12 | 24 |
| Blank | — | 205 ± 3 | 209 ± 4 (3.6 ± 2.8) | 205 ± 4 (0.1 ± 2.2) | 206 ± 6 (0.7 ± 3.2) | 204 ± 5 (−1.6 ± 3.1) | 207 ± 4 (1.6 ± 3.0) | 206 ± 4 (0.6 ± 2.1) |
| Can | 0.36 | 203 ± 4 | 201 ± 3 (−2.0 ± 3.6) | 192 ± 4 (−11.0 ± 1.2**) | 185 ± 6 (−17.7 ± 2.9**) | 196 ± 3 (−7.3 ± 2.8) | 199 ± 3 (−3.7 ± 2.9) | 204 ± 3 (1.4 ± 0.7) |
| Chl | 0.36 | 205 ± 4 | 204 ± 4 (−1.4 ± 1.0) | 205 ± 4 (−0.6 ± 0.6) | 204 ± 4 (−1.3 ± 0.6) | 204 ± 4 (−1.3 ± 0.6) | 204 ± 3 (−1.4 ± 1.0) | 205 ± 4 (−0.4 ± 0.7) |
| F2 | 0.36 + 0.36 | 207 ± 4 | 202 ± 4 (−4.9 ± 0.7*#) | 197 ± 3 (−10.0 ± 0.6**####) | 186 ± 5 (−21.0 ± 1.9***####) | 189 ± 4 (−17.9 ± 2.8***+###) | 194 ± 4 (−12.1 ± 1.5**+####) | 198 ± 3 (−8.9 ± 1.6**+++####) |

Notes:
1. Values in the brackets are the difference values compared with the basic value;
2. Compared with the blank control group, *P < 0.05, P < 0.01, *P < 0.001;
3. Compared with Can, +P < 0.05, +++P < 0.001;
4. Compared with Chl, #P < 0.05, ###P < 0.001.

EXAMPLE 3

Influence of 0.54 mg/kg of Chlorthalidone and 0.36 mg/kg of Candesartan Cilexetil and Pharmaceutical Compositions Thereof on SBP It still has an antihypertensive effect before administration of pharmaceutical composition 3 (F3), and after administration, the effect may last 24 hours, and the duration of antihypertension is significantly prolonged. Statistical analysis shows that chlorthalidone and candesartan cilexetil have a synergistic effect in the duration of antihypertension; the antihypertensive effect of F3 is better than that of candesartan cilexetil after administration for 8 to 24 h and is better than that of chlorthalidone before administration and after administration for 2 to 24 h. Statistical analysis shows that chlorthalidone and candesartan cilexetil have a synergistic effect in the degree of the blood pressure reduction after administration for 24 h (P=0.008), and the results are shown in Table 3.

EXAMPLE 4

Influence of 0.72 mg/kg of Chlorthalidone and 0.36 mg/kg of Candesartan Cilexetil and Pharmaceutical Compositions Thereof on SBP It still has an antihypertensive effect before administration of the pharmaceutical composition 4 (F4), and after administration, the effect may last 24 hours, and the duration of antihypertension is significantly prolonged. Statistical analysis shows that chlorthalidone and candesartan cilexetil have a synergistic effect in the duration of antihypertension; the antihypertensive effect of F4 is better than that of candesartan cilexetil after administration for 8 to 24 hours and is better than that of chlorthalidone before administration and after administration for 2 to 24 hours. Statistical analysis shows that chlorthalidone and candesartan cilexetil have a synergistic effect in the degree of the blood pressure reduction after administration for 24 hours (P=0.0021), and the results are shown in Table 4.

TABLE 3

($\bar{x} \pm SE$, n = 7)

| Group | Dosage (mg/kg) | Basic value | Pre-admin- istration | After administration (h) | | | | |
|---|---|---|---|---|---|---|---|---|
| | | | | 2 | 4 | 8 | 12 | 24 |
| Blank | — | 205 ± 3 | 209 ± 4 (3.6 ± 2.8) | 205 ± 4 (0.1 ± 2.2) | 206 ± 6 (0.7 ±) | 204 ± 5 (−1.6 ± 3.1) | 207 ± 4 (1.6 ± 3.0) | 206 ± 4 (0.6 ± 2.1) |
| Can | 0.36 | 203 ± 4 | 201 ± 3 (−2.0 ± 3.6) | 192 ± 4 (−11.0 ± 1.2**) | 185 ± 6 (−17.7 ± 2.9**) | 196 ± 3 (−7.3 ± 2.8) | 199 ± 3 (−3.7 ± 2.9) | 204 ± 3 (1.4 ± 0.7) |
| Chl | 0.36 | 204 ± 5 | 203 ± 5 (−1.6 ± 0.4) | 202 ± 5 (−2.0 ± 1.0) | 202 ± 5 (−2.0 ± 0.6) | 201 ± 5 (−3.7 ± 0.4) | 203 ± 4 (−1.9 ± 0.8) | 202 ± 5 (−2.6 ± 0.7) |
| F3 | 0.36 + 0.54 | 208 ± 4 | 203 ± 4 4 (−5.1 ± 1.0*##) | 197 ± 4 (−11.7 ± 1.7**####) | 185 ± 4 (−22.9 ± 0.8***####) | 187 ± 4 (−21.0 ± 1.7**++###) | 192 ± 4 (−15.9 ± 1.5***+###) | 197 ± 4 (−11.0 ± 2.2**+++##) |

Notes:
1. Values in the brackets are the difference values compared with the basic value;
2. Compared with the blank control group, *P < 0.05, P < 0.01, *P < 0.001;
3. Compared with Can, +P < 0.05, +++P < 0.001;
4. Compared with Chl, ##P < 0.01, ###P < 0.001.

TABLE 4

($\bar{x} \pm SE$, n = 7)

| Group | Dosage (mg/kg) | Basic value | Pre-administration | After administration (h) 2 | 4 |
|---|---|---|---|---|---|
| Blank | — | 205 ± 3 | 209 ± 4 (3.6 ± 2.8) | 205 ± 4 (0.1 ± 2.2) | 206 ± 6 (0.7 ± 3.2) |
| Can | 0.36 | 203 ± 4 | 201 ± 3 (−2.0 ± 3.6) | 192 ± 4 (−11.0 ± 1.2**) | 185 ± 6 (−17.7 ± 2.9**) |
| Chl | 0.36 | 207 ± 4 | 205 ± 4 (−2.3 ± 0.4) | 203 ± 4 (−3.9 ± 0.6) | 202 ± 4 (−4.9 ± 0.4) |
| F4 | 0.36 + 0.72 | 208 ± 4 | 202 ± 4 (−6.0 ± 0.6*###) | 197 ± 4 (−11.6 ± 0.9**###) | 185 ± 4 (−23.6 ± 1.3***###) |

| Group | After administration (h) 8 | 12 | 24 |
|---|---|---|---|
| Blank | 204 ± 5 (−1.6 ± 3.1) | 207 ± 4 (1.6 ± 3.0) | 206 ± 4 (0.6 ± 2.1) |
| Can | 196 ± 3 (−7.3 ± 2.8) | 199 ± 3 (−3.7 ± 2.9) | 204 ± 3 (1.4 ± 0.7) |
| Chl | 202 ± 4 (−4.9 ± 0.5) | 205 ± 4 (−2.6 ± 0.8) | 205 ± 3 (−2.4 ± 1.2) |
| F4 | 185 ± 5 (−23.0 ± 0.8***+++###) | 191 ± 4 (−17.3 ± 0.7***+++###) | 195 ± 5 (−13.1 ± 2.2**+++###) |

Notes:
1. Values in the brackets are the difference values compared with the basic value;
2. Compared with the blank control group, *P < 0.05, P < 0.01, *P < 0.001;
3. Compared with Can, +++P < 0.001;
4. Compared with Chl, ##P < 0.01, ###P < 0.001.

EXAMPLE 5

Influence of 1.125 mg/kg of Chlorthalidone and 0.36 mg/kg of Candesartan Cilexetil and Pharmaceutical Compositions Thereof on SBP 1.125 mg/kg of chlorthalidone has an antihypertensive effect 4 hours after administration.

It still has an antihypertensive effect before administration of pharmaceutical composition 5 (F5), and after administration, the effect can last 24 hours, and the duration of antihypertension is significantly prolonged. Statistical analysis shows that chlorthalidone and candesartan cilexetil have a synergistic effect in the duration of antihypertension; the antihypertensive effect of F5 is better than that of candesartan cilexetil after administration for 2 hours and 8-24 hours, and is also better than that of chlorthalidone after administration for 2 to 24 hours. Statistical analysis shows that chlorthalidone and candesartan cilexetil have a synergistic effect in the degree of the blood pressure reduction after administration for 24 hours (P=0.0003), and the results are shown in Table 5.

TABLE 5

($\bar{x} \pm SE$, n = 7)

| Group | Dosage (mg/kg) | Basic value | Pre-administration | After administration (h) 2 | 4 | 8 | 12 | 24 |
|---|---|---|---|---|---|---|---|---|
| Blank | — | 205 ± 3 | 209 ± 4 (3.6 ± 2.8) | 205 ± 4 (0.1 ± 2.2) | 206 ± 6 (0.7 ± 3.2) | 204 ± 5 (−1.6 ± 3.1) | 207 ± 4 (1.6 ± 3.0) | 206 ± 4 (0.6 ± 2.1) |
| Can | 0.36 | 203 ± 4 | 201 ± 3 (−2.0 ± 3.6) | 192 ± 4 (−11.0 ± 1.2**) | 185 ± 6 (−17.7 ± 2.9**) | 196 ± 3 (−7.3 ± 2.8) | 199 ± 3 (−3.7 ± 2.9) | 204 ± 3 (1.4 ± 0.7) |
| Chl | 1.125 | 208 ± 4 | 206 ± 5 (−1.7 ± 1.8) | 205 ± 6 (−2.9 ± 2.6) | 199 ± 5 (−8.9 ± 1.2*) | 201 ± 5 (−6.3 ± 3.6) | 202 ± 4 (−6.0 ± 0.7) | 207 ± 4 (−0.4 ± 1.0) |
| F5 | 0.36 + 1.125 | 209 ± 5 | 201 ± 4 (−7.9 ± 2.3*) | 191 ± 5 (−18.1 ± 1.6**+###) | 185 ± 5 (−24.1 ± 2.9**###) | 185 ± 6 (−24.3 ± 2.9***+###) | 189 ± 4 (−20.6 ± 2.3***+++###) | 196 ± 4 (−13.1 ± 2.1**+++###) |

Notes:
1. Values in the brackets are the difference values compared with the basic value;
2. Compared with the blank control group, *P < 0.05, P < 0.01, *P < 0.001;
3. Compared with Can, ++P < 0.01, +++P < 0.001;
4. Compared with Chl, ##P < 0.01, ###P < 0.001.

EXAMPLE 6

Influence of 2.25 mg/kg of Chlorthalidone and 0.36 mg/kg of Candesartan Cilexetil and Pharmaceutical Compositions Thereof on SBP 2.25 mg/kg of chlorthalidone has a significant antihypertensive effect after administration for 2 to 12 hours.

It already has an antihypertensive effect before administration of pharmaceutical composition 6 (F6), and the effect may last 24 hours after the administration. Statistical analysis shows that chlorthalidone and candesartan cilexetil have a synergistic effect in the duration of antihypertension; the antihypertensive effect of F6 is better than that of candesartan cilexetil after administration for 2 to 24 hours and is also better than that of chlorthalidone before administration and after administration for 2 to 24 hours. Chlorthalidone and candesartan cilexetil have a synergistic effect in the antihypertensive effect after administration for 24 hours (P=0.0008). The results are shown in Table 6.

influence on the maximum reduction of SBP and the AUC, and 1.125 and 2.25 mg/kg of chlorthalidone can cause significant decrease of both the maximum reduction of SBP and the AUC.

The influences of F1, F2, F3, F4, F5 and F6 on both the maximum reduction of SBP and the AUC are better than those of the corresponding component chlorthalidone; the influences of F4, F5 and F6 on the maximum reduction of SBP is better than that of candesartan cilexetil, and the influences of F1, F2, F3, F4, F5 and F6 on AUC is better than that of candesartan cilexetil.

From the influence of F1, F2, F3, F4, F5 and F6 on AUC, it can be seen that candesartan cilexetil and chlorthalidone in all of the three pharmaceutical compositions have synergistic effects. The results are shown in Table 7.

TABLE 6

($\bar{x} \pm SE, n = 7$)

| Group | Dosage (mg/kg) | Basic value | Pre-administration | After administration (h) 2 | 4 |
|---|---|---|---|---|---|
| Blank | — | 205 ± 3 | 209 ± 4 (3.6 ± 2.8) | 205 ± 4 (0.1 ± 2.2) | 206 ± 6 (0.7 ± 3.2) |
| Can | 0.36 | 203 ± 4 | 201 ± 3 (−2.0 ± 3.6) | 192 ± 4 (−11.0 ± 1.2**) | 185 ± 6 (−17.7 ± 2.9**) |
| Chl | 2.25 | 207 ± 5 | 205 ± 4 (−1.3 ± 1.8) | 198 ± 6 (−8.3 ± 2.0*) | 192 ± 6 (−11.3 ± 2.8*) |
| F6 | 0.36 + 2.25 | 208 ± 4 | 198 ± 3 (−10.1 ± 1.5**##) | 187 ± 4 (−20.6 ± 1.9***++###) | 179 ± 5 (−28.4 ± 2.9***+##) |

| Group | After administration (h) 8 | 12 | 24 |
|---|---|---|---|
| Blank | 204 ± 5 (−1.6 ± 3.1) | 207 ± 4 (1.6 ± 3.0) | 206 ± 4 (0.6 ± 2.1) |
| Can | 196 ± 3 (−7.3 ± 2.8) | 199 ± 3 (−3.7 ± 2.9) | 204 ± 3 (1.4 ± 0.7) |
| Chl | 195 ± 4 (−11.1 ± 2.1*) | 197 ± 5 (−9.4 ± 1.6*) | 202 ± 4 (−4.6 ± 2.2) |
| F6 | 181 ± 3 (−26.4 ± 1.3***+++###) | 186 ± 4 (−22.1 ± 1.9***+++###) | 191 ± 4 (−16.4 ± 1.0***+++###) |

Notes:
1. Values in the brackets are the difference values compared with the basic value;
2. Compared with the blank control group, *P < 0.05, P < 0.01, *P < 0.001;
3. Compared with Can, +P < 0.05, ++P < 0.01, +++P < 0.001;
4. Compared with Chl, ##P < 0.01, ###P < 0.001.

EXAMPLE 7

Influence of Chlorthalidone and Candesartan Cilexetil and Pharmaceutical Compositions Thereof on the Maximum Reduction of SBP and the AUC As compared with the blank control group, 0.36 mg/kg of candesartan cilexetil can result in a maximum reduction of SBP up to 19.0 mmHg and a AUC up to −127 mmHg·h.

As compared with the blank control group, 0.0675, 0.36, 0.54 and 0.72 mg/kg of chlorthalidone have no significant

TABLE 7

($\bar{x} \pm SE, n = 7$)

| Group | Dosage (mg/kg) | maximum reduction of the blood pressure (mmHg) | $AUC_{0-24h}$ (mmHg·h) |
|---|---|---|---|
| Blank | — | −4.1 ± 2.8 | −27.1 ± 30.9 |
| Can | 0.36 | −19.0 ± 2.4* | −127.0 ± 36.0 |
| Chl | 0.0675 | −4.7 ± 1.3 | −9.0 ± 26.0 |
| F1 | 0.36 + 0.0675 | −21.0 ± 3.4*## | −240.0 ± 28.5***+### (having a synergistic effect P = 0.0439) |

TABLE 7-continued ($\bar{x} \pm SE$, n = 7)

| Group | Dosage (mg/kg) | maximum reduction of the blood pressure (mmHg) | $AUC_{0-24h}$ (mmHg · h) |
|---|---|---|---|
| Chl | 0.36 | −3.7 ± 0.5 | −26.0 ± 8.9 |
| F2 | 0.36 + 0.36 | −22.4 ± 2.2,*,### | −277.0 ± 32.9**,+,### (having a synergistic effect P = 0.0168) |
| Chl | 0.54 | −4.7 ± 0.3 | −57.0 ± 7.2 |
| F3 | 0.36 + 0.54 | −23.7 ± 1.2***,### | −374.0 ± 32.4***,+++,### (having a synergistic effect P = 0.001) |
| Chl | 0.72 | −5.7 ± 0.6 | −79.0 ± 14.9 |
| F4 | 0.36 + 0.72 | −25.1 ± 0.8***,+,### | −409.0 ± 18.1***,+++,### (having a synergistic effect P = 0.0002) |
| Chl | 1.125 | −12.0 ± 2.0** | −110.0 ± 24.0* |
| F5 | 0.36 + 1.125 | −26.9 ± 2.6**,+,### | −457.0 ± 36.8***,+++,### (having a synergistic effect P = 0.0009) |
| Chl | 2.25 | −15.0 ± 1.1**,++ | −199.0 ± 36.0* |
| F6 | 0.36 + 2.25 | −30.7 ± 2.1***,+++,### | −518.0 ± 24.6***,+++,### (having a synergistic effect P = 0.0024) |

Notes:
1. Compared with the blank control group, *P < 0.05, P < 0.01, *P < 0.001;
2. Compared with Can, +P < 0.05, ++P < 0.01, +++P < 0.001;
3. Compared with corresponding Chl, ##P < 0.01, ###P < 0.001.

Results Analysis of Examples 1-7

The antihypertensive effect of the pharmaceutical composition F1, i.e., Can:Chl=5.3:1 (0.36:0.0675 mg/kg) is better than that of candesartan cilexetil after administration for 24 hours and is better than that of chlorthalidone after administration for 2 to 24 hours. Chlorthalidone and candesartan cilexetil have a synergistic effect in antihypertension after administration for 24 hours (P=0.036) and also have a synergistic effect in the influence on AUC after administration for 24 hours (P=0.0439).

The antihypertensive effect of the pharmaceutical composition F2, i.e., Can:Chl=1:1 (0.36:0.36 mg/kg) is better than that of candesartan cilexetil after administration for 8 to 24 hours and is better than that of chlorthalidone after administration for 2 to 24 hours. Chlorthalidone and candesartan cilexetil have a synergistic effect in the degree of blood pressure reduction after administration for 24 hours (P=0.0031) and also have a synergistic effect in the influence on AUC after administration for 24 hours (P=0.0168).

The antihypertensive effect of the pharmaceutical composition F3, i.e., Can:Chl=1:1.5 (0.36:0.54 mg/kg) is better than that of candesartan cilexetil after administration for 8 to 24 hours and is better than that of chlorthalidone before administration and after administration for 2 to 24 hours. Chlorthalidone and candesartan cilexetil have a synergistic effect in the degree of blood pressure reduction after administration for 24 hours (P=0.008) and also have a synergistic effect in the influence on AUC after administration for 24 hours (P=0.001).

The antihypertensive effect of the pharmaceutical composition F4, i.e., Can:Chl=1:2 (0.36:0.72 mg/kg) is better than that of candesartan cilexetil after administration for 8 to 24 hours and is better than that of chlorthalidone before administration and after administration for 2 to 24 hours. Chlorthalidone and candesartan cilexetil have a synergistic effect in the degree of blood pressure reduction after administration for 24 hours (P=0.0021) and also have a synergistic effect in the influence on AUC after administration for 24 hours (P=0.0002).

The antihypertensive effect of the pharmaceutical composition F5, i.e., Can:Chl=1:3.125 (0.36:1.125 mg/kg) is better than that of candesartan cilexetil after administration for 2 hours and 8 to 24 hours and is better than that of chlorthalidone after administration for 2 to 24 hours. Chlorthalidone and candesartan cilexetil have a synergistic effect in the degree of blood pressure reduction after administration for 24 hours (P=0.0003). Chlorthalidone and candesartan cilexetil also have a synergistic effect in the influence on AUC after administration for 24 hours (P=0.0009).

The antihypertensive effect of the pharmaceutical composition F6, i.e., Can:Chl=1:6.25 (0.36:2.25 mg/kg) is better than that of candesartan cilexetil and is also better than that of chlorthalidone after administration for 2 to 24 hours. Chlorthalidone and candesartan cilexetil have a synergistic effect in antihypertension after administration for 24 hours (P=0.0008). Chlorthalidone and candesartan cilexetil also have a synergistic effect in the influence on AUC after administration for 24 hours (P=0.0009).

The AUC (−240.0±28.5) of the pharmaceutical composition F1, i.e., Can:Chl=5.3:1 (0.36:0.0675 mg/kg) is smaller than the AUC (−374.0±32.4) of the pharmaceutical composition F3, i.e., Can:Chl=1:1.5 (0.36:0.54 mg/kg), the AUCs of both F1 and F3 have a significant difference (P=0.0092). The synergistic effect of the pharmaceutical composition with 5.3:1 of Can:Chl is weaker than the synergistic effect of the pharmaceutical composition with 1:1.5 of Can:Chl, i.e., the drug combination with a ratio of 1:1.5 is better than the drug combination with a ratio of 5.3:1.

The AUC (−457.0±36.8) of the pharmaceutical composition F5, i.e., Can:Chl=1:3.125 (0.36:1.125 mg/kg) has no significant difference as compared with the AUC (−518.0±24.6) of the pharmaceutical composition F6, i.e., Can:Chl=1:6.25 (0.36:2.25 mg/kg) (P=0.1942). According to the clinical medication practice, however, in certain conditions, the side effects such as electrolyte disturbance caused by the pharmaceutical composition with higher proportion of chlorthalidone are higher than those caused by the pharmaceutical composition with lower proportion of chlorthalidone. Therefore, in the case of having similar efficacy, the pharmaceutical composition with lower proportion of chlorthalidone should be preferred, i.e., the drug combination ratio of 1:3.125 is better than the drug combination ratio of 1:6.25.

EXAMPLE 8

0.1 mg/kg of Candesartan Cilexetil and 0.625 mg/kg of Chlorthalidone and Pharmaceutical Composition Thereof (the Ratio of Candesartan Cilexetil to Chlorthalidone is 1:6.25)

Both of the single drugs, Can and Chl, as well as the combination of Can-Chl can decrease $AUC_{0-24h}$ and $AUC_{0-14d}$. With such a ratio and dosages, candesartan cilexetil and chlorthalidone have a significant synergistic effect in the $AUC_{0-24h}$, and they also have a significant synergistic effect on $AUC_{0-14d}$. The results are shown in Table 8.

TABLE 8

($\bar{x} \pm SE$, n = 8-10)

| Drugs | Dosage(mg/kg) | $AUC_{0-24h}$(mmHg · h) | $AUC_{0-14d}$(mmHg · d) |
|---|---|---|---|
| Blank | 0 | 107.3 ± 129.7 | 55.3 ± 70.9 |
| Can | 0.1 | −209.1 ± 86.8*** | −149.9 ± 85.7*** |
| Chl | 0.625 | −190.4 ± 80.7*** | −134.5 ± 70.1*** |
| Can-Chl | 0.1/0.625 | −468.2 ± 119.6***$ (synergistic) | −338.3 ± 101.2***$ (synergistic) |

Note:
Compared with the blank control group: ***P < 0.001; factorial analysis of variance: $P < 0.05.

EXAMPLE 9

Synergistic Effect of Candesartan Cilexetil and Chlorthalidone with the Ratio of 1:3.125

(1) 0.2 mg/kg of Candesartan Cilexetil and 0.625 mg/kg of Chlorthalidone and Pharmaceutical Composition Thereof.

Both of the single drugs, Can or Chl, as well as the combination of Can-Chl can decrease $AUC_{0-24h}$ and $AUC_{0-14d}$. With such a ratio and dosages, candesartan cilexetil and chlorthalidone have a significant synergistic effect on $AUC_{0-24h}$ and $AUC_{0-14d}$. The results are shown in Table 9.

TABLE 9

($\bar{x} \pm SE$, n = 8-10)

| Drugs | Dosage(mg/kg) | $AUC_{0-24h}$(mmHg · h) | $AUC_{0-14d}$(mmHg · d) |
|---|---|---|---|
| Blank | 0 | 107.3 ± 129.7 | 55.3 ± 70.9 |
| Can | 0.2 | −237.7 ± 91.6*** | −173.1 ± 37.5*** |
| Chl | 0.625 | −190.4 ± 80.7*** | −134.5 ± 70.1*** |
| Can-Chl | 0.2/0.625 | −485.7 ± 140.0***$ (synergistic) | −361.6 ± 148.0***$ (synergistic) |

Note:
Compared with the blank control group: ***P < 0.001; factorial analysis of variance: $P < 0.05.

(2) 0.4 mg/kg of Candesartan Cilexetil and 1.25 mg/kg of Chlorthalidone and Pharmaceutical Composition Thereof.

Both of the single drugs, Can and Chl, as well as the combination of Can-Chl can decrease $AUC_{0-24h}$ and $AUC_{0-14d}$. With such a ratio and dosages, candesartan cilexetil and chlorthalidone have a significant synergistic effect on $AUC_{0-24h}$ and $AUC_{0-14d}$. The results are shown in Table 10.

TABLE 10

($\bar{x} \pm SE$, n = 8-10)

| Drugs | Dosage(mg/kg) | $AUC_{0-24h}$(mmHg · h) | $AUC_{0-14d}$(mmHg · d) |
|---|---|---|---|
| Blank | 0 | 107.3 ± 129.7 | 55.3 ± 70.9 |
| Can | 0.4 | −326.0 ± 76.3*** | −227.3 ± 79.6*** |
| Chl | 1.25 | −208.1 ± 164.5*** | −174.2 ± 93.0*** |
| Can-Chl | 0.4/1.25 | −599.3 ± 58.6***$ (synergistic) | −417.9 ± 55.0***$ (synergistic) |

Note:
Compared with the blank control group: ***P < 0.001; factorial analysis of variance: $P < 0.05.

EXAMPLE 10

Synergistic Effect of Candesartan Cilexetil and Chlorthalidone with the Ratio of 1:1.5625

(1) 0.2 mg/kg of Candesartan Cilexetil and 0.3125 mg/kg of Chlorthalidone and Pharmaceutical Composition Thereof.

Both of the single drugs, Can and Chl, as well as the combination of Can-Chl can decrease $AUC_{0-24h}$ and $AUC_{0-14d}$. With such a ratio and dosages, candesartan cilexetil and chlorthalidone have a significant synergistic effect on $AUC_{0-24h}$ and $AUC_{0-14d}$. The results are shown in Table 11.

TABLE 11

($\bar{x} \pm SE$, n = 8-10)

| Drugs | Dosage(mg/kg) | $AUC_{0-24h}$(mmHg · h) | $AUC_{0-14d}$(mmHg · d) |
|---|---|---|---|
| Blank | — | 107.3 ± 129.7 | 55.3 ± 70.9 |
| Can | 0.2 | −237.7 ± 91.6*** | −173.1 ± 37.5*** |
| Chl | 0.3125 | −133.1 ± 53.9*** | −125.9 ± 50.0*** |
| Can-Chl | 0.2/0.3125 | −617.6 ± 93.7***$ (synergistic) | −434.9 ± 111.9***$ (synergistic) |

Note:
Compared with the blank control group: ***P < 0.001; factorial analysis of variance: $P < 0.05.

(2) 0.4 mg/kg of Candesartan Cilexetil and 0.625 mg/kg of Chlorthalidone and Pharmaceutical Composition Thereof.

Both of the single drugs, Can and Chl, as well as the combination of Can-Chl can decrease $AUC_{0-24h}$ and $AUC_{0-14d}$. With such a ratio and dosages, candesartan cilexetil and chlorthalidone have a significant synergistic effect on $AUC_{0-24h}$ and $AUC_{0-14d}$. The results are shown in Table 12.

TABLE 12

($\bar{x} \pm SE$, n = 8-10)

| Drugs | Dosage(mg/kg) | $AUC_{0-24h}$(mmHg · h) | $AUC_{0-14d}$(mmHg · d) |
|---|---|---|---|
| Blank | Blank | 107.3 ± 129.7 | 55.3 ± 70.9 |
| Can | 0.4 | −326 ± 76.3*** | −227.3 ± 79.6*** |
| Chl | 0.625 | −190.4 ± 80.7*** | −134.5 ± 70.1*** |
| Can-Chl | 0.4/0.625 | −644.9 ± 117.0***$$ (synergistic) | −460.7 ± 143.7***$ (synergistic) |

Note:
Compared with the blank control group: ***P < 0.001; factorial analysis of variance: $P < 0.05, $$P < 0.01.

EXAMPLE 11

0.4 mg/kg of Candesartan Cilexetil and 0.3125 mg/kg of Chlorthalidone and Pharmaceutical Composition Thereof (the Ratio of Candesartan Cilexetil to Chlorthalidone is 1.28:1)

Both of the single drug, Can and Chl, as well as the combination of Can-Chl can decrease $AUC_{0-24h}$ and $AUC_{0-14d}$. With such a ratio and dosages, candesartan cilexetil and chlorthalidone have a significant synergistic effect on $AUC_{0-24h}$ and $AUC_{0-14d}$. The results are shown in Table 13.

TABLE 13

($\bar{x} \pm SE$, n = 8-10)

| Drugs | Dosage(mg/kg) | $AUC_{0-24h}$(mmHg · h) | $AUC_{0-14d}$(mmHg · d) |
|---|---|---|---|
| Blank | — | 107.3 ± 129.7 | 55.3 ± 70.9 |
| Can | 0.4 | −326.0 ± 76.3*** | −227.3 ± 79.6*** |
| Chl | 0.3125 | −133.1 ± 53.9*** | −125.9 ± 50.0*** |
| Can-Chl | 0.4/0.3125 | −531.7 ± 65.6***$ (synergistic) | −424.0 ± 67.0***$ (synergistic) |

Note:
Compared with the blank control group: ***P < 0.001; factorial analysis of variance: $P < 0.05.

EXAMPLE 12

0.4 mg/kg of Candesartan Cilexetil and 0.15625 mg/kg of Chlorthalidone and Pharmaceutical Composition Thereof (the Ratio of Candesartan Cilexetil to Chlorthalidone is 2.56:1)

Both of the single drugs Can and Chl, as well as the combination of Can-Chl can decrease $AUC_{0-24h}$ and $AUC_{0-14d}$. With such a ratio and dosages, candesartan cilexetil and chlorthalidone have a significant synergistic effect on $AUC_{0-24h}$ and $AUC_{0-14d}$. The results are shown in Table 14.

TABLE 14

($\bar{x} \pm SE$, n = 8-10)

| Drugs | Dosage(mg/kg) | $AUC_{0-24h}$(mmHg · h) | $AUC_{0-14d}$(mmHg · d) |
|---|---|---|---|
| Blank | — | 107.3 ± 129.7 | 55.3 ± 70.9 |
| Can | 0.4 | −326.0 ± 76.3*** | −227.3 ± 79.6*** |
| Chl | 0.15625 | −47.0 ± 23.5** | −36.0 ± 23.8** |
| Can-Chl | 0.4/0.15625 | −446.8 ± 108.4***$ (synergistic) | −367.4 ± 83.1***$ (synergistic) |

Note:
Compared with the blank control group: P < 0.01, *P < 0.001; factorial analysis of variance: $P < 0.05.

Results Analysis of Examples 8-12:

Examples 8-12 illustrate the synergistic effect of the combination with dosage ratios around the clinical single-drug specification. For a same combination ratio, different combination dosages for experiment are set in connection with the pharmacological property of drug action to reflect the interaction of the drugs objectively and accurately. Studies show that:

1) Can-Chl with the combination ratio of 1:3.125, single dose and continuous administration for 14 d has a good synergistic effect. This combination ratio can represent the clinical combination dosages of 4/12.5, 8/25 and 16/50 mg.

2) Can-Chl with the combination ratio of 1:1.5625, single dose and continuous administration for 14 d has a good synergistic effect. This combination ratio can represent the clinical combination dosages of 8/12.5 and 16/25 mg.

3) Can-Chl with the combination ratio of 1.28:1, single dose and continuous administration for 14 d has a good synergistic effect. This combination ratio can represent the clinical combination dosages of 16/12.5 and 32/25 mg.

4) Can-Chl with the combination ratio of 2.56:1, single dose and continuous administration for 14 d has certain synergistic effect. This combination ratio can represent the clinical combination dosages of 16/6.25 and 32/12.5 mg.

5) When the dose level of Can is at 0.4 mg/kg and the dosage of Chl is increased from 0.62 mg/kg to 1.25 mg/kg, i.e., when the ratio of Can to Chl is increased from 1:1.5625 to 1:3.125, the antihypertensive effect does not increase, which suggests that at this dose level, the ratio of 1:1.5625 is better than the ratio of 1:3.125. When the dose level of Can is at 0.4 mg/kg and the dosage of Chl is increased, i.e., during the ratio of Can to Chl increasing from 2.56:1 to 1:3.125, the antihypertensive effect increases, which suggests that at this dose level, the ratios of 1:1.5625 and 1:3.125 are better than the ratio of 1.28:1, and the ratio of 1.28:1 is better than the ratio of 2.56:1.

In a word, with the combination ratio of Can-Chl being 1:3.125, 1:1.5625, 1.28:1 and 2.56:1, the combination therapy of Can and Chl has a synergistic effect in antihypertension, suggesting that when Can and Chl are combined at the clinical combination dosages of 4/12.5, 8/25, 16/50, 8/12.5, 16/25, 16/12.5, 32/25, 16/6.25 or 32/12.5 mg, the combination has a synergistic effect.

EXAMPLE 13

Comparison of the Effects of the Combination of Candesartan Cilexetil-Chlorthalidone (Can-Chl) with the Combination of Candesartan Cilexetil-Hydrochlorothiazide (Can-HCTZ)

Combination of Can-Chl: 0.39 mg/kg of candesartan cilexetil+0.609375 mg/kg of chlorthalidone;
Combination of Can-HCTZ: 0.39 mg/kg of candesartan cilexetil+0.609375 mg/kg of hyderochlorothiazide.

(1) Influences on AUC and the Effect of the Maximum Reduction Value of Blood Pressure Both of the combinations can decrease $AUC_{0-24h}$. The extents of $AUC_{0-14d}$ decreased by the combinations of Can-Chl are all higher than those decreased by the combinations of Can-HCTZ with corresponding combination ratio. The influence of the combination of Can-Chl on the maximum reduction value of blood pressure from 0 to 14 d is better than the combination of Can-HCTZ with corresponding combination ratio. The results are shown in Table 15.

TABLE 15

($\bar{x} \pm SE$, n = 6)

| Group | Blank | Can-Chl | Can-HCTZ |
|---|---|---|---|
| Dosage (mg/kg) | — | 0.39/0.609375 | 0.39/0.609375 |
| $AUC_{0-24h}$ (mmHg · h) | −1.5 ± 235.3 | −661.9 ± 128.1*** | −528.7 ± 111.1*** |
| $AUC_{0-14d}$ (mmHg · d) | 12.8 ± 112.5 | −465.2 ± 61.3***+ | −366.6 ± 73.6*** |
| $Max_{0-14d}$ (mmHg) | −13.2 ± 7.9 | −43.2 ± 2.6***+ | −37.3 ± 4.9*** |

Note:
1. Compared with the blank control group: ***P < 0.001;
2. Compared with the Can-HCTZ group: +P < 0.05.

(2) Influences of Drug Withdrawal on SBP

After the combinations of Can-HCTZ withdrawing, the SBP is rising; whereas all of the SBPs after withdrawing the combinations of Can-Chl are lower than the SBPs after withdrawing the combinations of Can-HCTZ. The results are shown in Table 16 and FIG. 1.

TABLE 16

($\bar{x} \pm SE$, n = 6)

| Group | Blank | Can-Chl | Can-HCTZ |
|---|---|---|---|
| Dosage (mg/kg) | — | 0.39/0.609375 | 0.39/0.609375 |
| d1 | 11.3 ± 9.9 | −10.7 ± 4.5***+ | −3.3 ± 5.2** |
| d2 | 11.3 ± 5.8 | −10.3 ± 4.7***+ | 0.5 ± 10.7 |
| d3 | 9.2 ± 13.3 | −5.5 ± 7.2*++ | 4.8 ± 8.2 |

Note:
1. Compared with the blank control group: *P < 0.05, P < 0.01, *P < 0.001;
2. Compared with the Can-HCTZ group: +P < 0.05, ++P < 0.05.

Results Analysis of Example 13:

The effect of continuous administration of Can-Chl with the combination ratio of 1:1.5625, i.e., 0.39/0.609375 mg/kg on $AUC_{0-14d}$ is better than that of continuous administration of the combination of Can-HCTZ, and the influence of Can-Chl with the combination ratio of 1:1.5625 on the maximum reduction value of blood pressure is better than that of the combination of Can-HCTZ; the reducing effect on SBP after withdrawing Can-Chl with the combination ratio of 1:1.5625 for 3 days is better than that of the combination of Can-HCTZ having equal combination ratio; this combination ratio can represent the clinical combination dosage of 8/12.5 mg.

In a word, with the equal ratio (1:1.5625) and equal dosage, the combination of Can-Chl causes larger degree of blood pressure reduction, milder rebound after drug withdrawal, and has longer action time as compared with the combination of Can-HCTZ.

In conclusion, the compound composed of candesartan or ester thereof and chlorthalidone has a synergistic antihypertensive effect, and can increase the efficacy, enhance the antihypertensive effect and extend effective antihypertension time when the ratio of candesartan or ester thereof to chlorthalidone is in the range of 5.3:1 to 1:6.25. Studying on the pharmaceutical compositions with such ratios of candesartan or ester thereof to chlorthalidone provides a possibility of decreasing drug dosages and alleviating side effects, which facilitates the treatment of hypertensive diseases.

The invention claimed is:

1. A pharmaceutical composition comprising candesartan or ester thereof and chlorthalidone as active ingredients, wherein the weight ratio of candesartan or ester thereof to chlorthalidone is 1.28:1 or 1:1.5 to 1:6.25.

2. The pharmaceutical composition according to claim 1, wherein the weight ratio of candesartan or ester thereof to chlorthalidone is 1.28:1 or 1:1.5 to 1:3.125.

3. The pharmaceutical composition according to claim 1, wherein the ester of candesartan is candesartan cilexetil.

4. A method for treating hypertension, the method comprising administering a pharmaceutical composition according to claim 1 to a patient in need of treatment.

5. The method according to claim 4, wherein the administration dosage of candesartan or ester thereof is 0.057-0.228 mg/kg per day, and the administration dosage of chlorthalidone is 0.089-0.357 mg/kg per day.

* * * * *